United States Patent
Moore

(10) Patent No.: US 7,121,135 B2
(45) Date of Patent: Oct. 17, 2006

(54) METHOD AND DEVICE FOR DETERMINING THE PERMEATION OF A BARRIER LAYER

(75) Inventor: Rodney Moore, Kennesaw, GA (US)

(73) Assignee: Tetra Laval Holdings & Fiance S.A., (CH)

(*) Notice: Subject to any disclaimer, the term of this patent is extended or adjusted under 35 U.S.C. 154(b) by 34 days.

(21) Appl. No.: 10/478,060

(22) PCT Filed: Apr. 11, 2002

(86) PCT No.: PCT/EP02/04016

§ 371 (c)(1),
(2), (4) Date: May 6, 2004

(87) PCT Pub. No.: WO02/095369

PCT Pub. Date: Nov. 28, 2002

(65) Prior Publication Data
US 2004/0177676 A1 Sep. 16, 2004

(30) Foreign Application Priority Data
May 18, 2001 (DE) ................ 101 24 225

(51) Int. Cl.
*G01N 15/08* (2006.01)
(52) U.S. Cl. .......................................... 73/38
(58) Field of Classification Search ............ 73/38
See application file for complete search history.

(56) References Cited

U.S. PATENT DOCUMENTS

| | | | |
|---|---|---|---|
| 4,047,422 A * | 9/1977 | Lyssy | 73/38 |
| 4,118,972 A * | 10/1978 | Goeppner et al. | 73/40 |
| 4,391,128 A | 7/1983 | McWhorter | |
| 5,591,898 A | 1/1997 | Mayer | |
| 6,766,682 B1 * | 7/2004 | Engle et al. | 73/38 |
| 2002/0162384 A1 * | 11/2002 | Sharp et al. | 73/38 |
| 2002/0194899 A1 * | 12/2002 | Gebele et al. | 73/38 |

FOREIGN PATENT DOCUMENTS

| | | |
|---|---|---|
| CA | 2122250 A1 | 3/1994 |
| CH | 685887 A5 | 10/1995 |
| DE | 19642009 A1 | 4/1997 |
| DE | 19962303 A1 | 7/2001 |
| EP | 0 833 139 A2 | 4/1998 |
| WO | WO 01/48452 A2 | 7/2001 |

* cited by examiner

Primary Examiner—Hezron Williams
Assistant Examiner—John Fitzgerald
(74) Attorney, Agent, or Firm—Stevens & Showalter LLP

(57) ABSTRACT

The invention relates to a method for determining the permeation of a barrier layer on the surface of a container (1), wherein the container is placed inside a pressure-tight closeable vessel (5), is degasified after a conditioning period on the side comprising the barrier layer, the pressure is measured for the duration thereof and measuring data therefrom enables the permeation of the barrier layer to be determined. The permeation of a plurality of containers (1) can be determined for an industrial application in a consecutive manner in a relatively short period of time by using very simple measuring devices. The invention is characterized in that the pressure-tight closeable vessel (5) and the container (1) arranged therein are evacuated, the partial pressures of several substances emitted from the wall of the container are measured and the increase in the pressure-time-curve is determined, representing a direct measurement of the quality of the barrier layer.

20 Claims, 5 Drawing Sheets

METHOD AND DEVICE FOR DETERMINING THE PERMEATION OF A BARRIER LAYER

Figure 1:
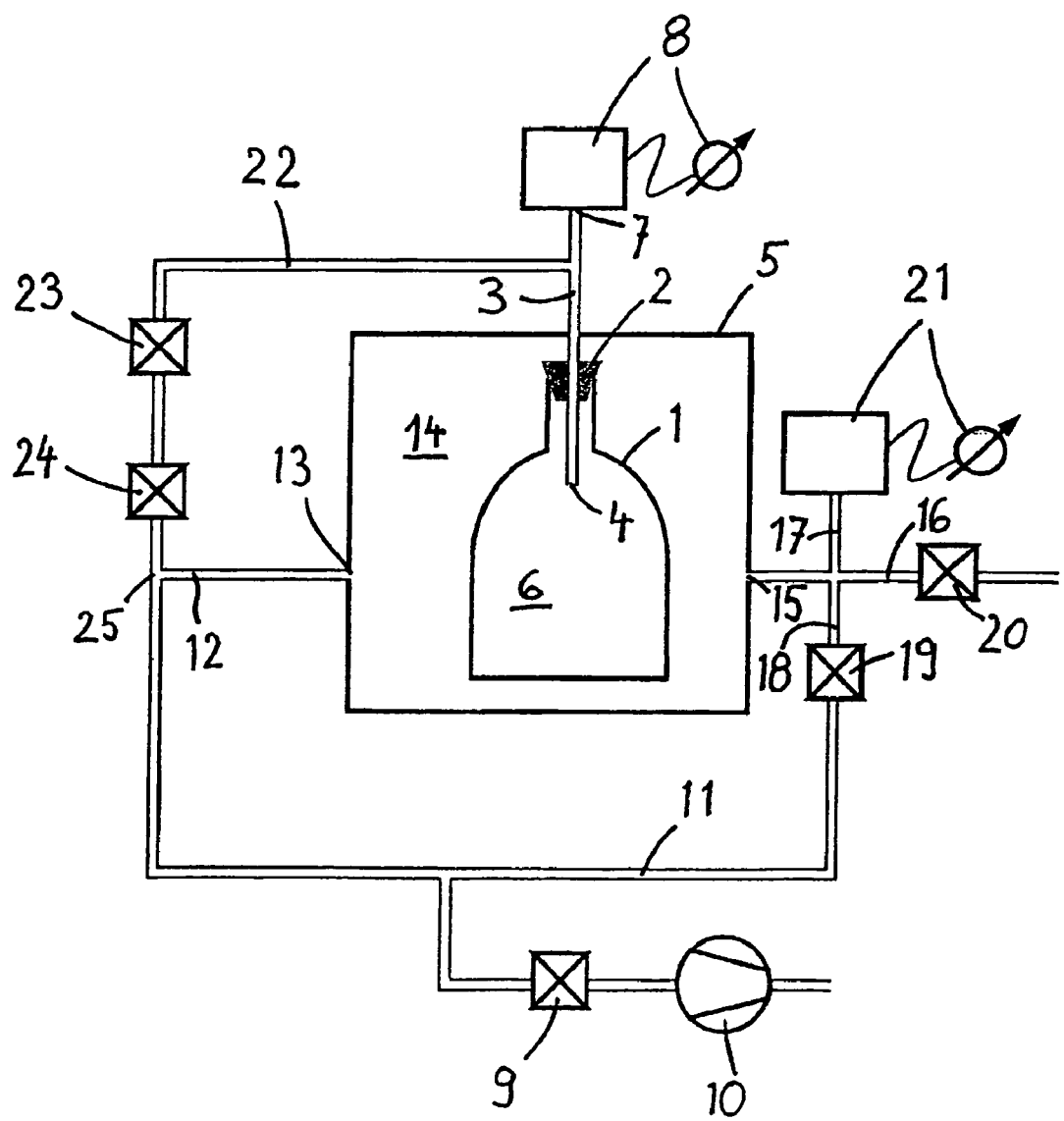

The invention concerns a method and an apparatus for determining the permeation of a barrier layer on the surface of a container, in which the container is put into a pressure-tightly closable vessel, it is left to degas after a conditioning time on the side with the barrier layer, the pressure in relation to time is measured and permeation of the barrier layer is determined from those measurement data.

It is known for fluid packs to be made from plastic material, for example in the form of bottles with an upwardly disposed opening. Such bottles are made from polyethylene terephthalate (PET) and are used in many cases for packaging for example water. It is known that the walls of the plastic packs are transmissive in respect of low-molecular gases, for which reason the periods of time for which fluid foodstuffs, in particular juices and $CO_2$-bearing mixed drinks, keep, are limited. In order to prevent the oxygen which is responsible for that from penetrating into the pack or to prevent carbon dioxide from escaping and thus to make such plastic packs better for use for fluid foodstuffs, the procedure has been adopted of providing the walls of such plastic packs with barrier layers, for example on the inside surface of plastic bottles.

It will be appreciated therefore that, when using plastic containers, in particular those consisting of PET, it is necessary to ensure that the wall has the highest possible barrier effect. Therefore, methods of measuring the barrier properties of a plastic wall have already been developed. Such a known method involves saturating for example a container wall to be measured and which acts as a barrier with a test gas and then, after the saturation step, allowing the substances which have been loaded into the container wall or material sample to outgas into a vessel which can be pressure-tightly closed. As a result, the partial pressure in question rises in that vessel and can be measured at certain time intervals. That affords a pressure-time curve from which it is possible to calculate the permeation or the permeability of the material to be investigated, with its barrier layer.

There is the disadvantage here that the procedure involving loading, degassing and measuring takes up to two hours so that this method is not suitable for industrial application in the production of plastic packs at a high level of output (large numbers of items per unit of time).

Therefore the object of the present invention is further to improve a determination method of the kind set forth in the opening part of this specification, in such a way that for industrial application it is possible to determine the permeation of a large number of containers in succession in a respectively shorter time than in 1–1½ hours and using simpler measuring devices.

The method and the apparatus according to the invention made industrial application their aim, wherein permeation of the barrier layer in question does not have to be measured in such an extravagant fashion that the measurement result satisfies highly qualified calibration conditions. On the contrary, it is sufficient for permeation of the layer in the respective container to be determined in such a way that it can or must be identified as good, adequate or defective.

In accordance with the invention, for the method, that object is attained in that the pressure-tightly closable vessel and the container disposed therein are evacuated, the partial pressures of a plurality of substances emitted from the container wall are measured and the gradient of the pressure-time curve which represents a direct measurement in respect of the quality of the barrier layer is ascertained. The method according to the invention can be used in particular for barrier layers which are disposed on the inside surface of a container, for example an inside of a pack. In that respect, particular attention in terms of executing the method is paid to packs of plastic material, in particular in the form of an upwardly open bottle. In the case of such a bottle-shaped container, the interior thereof can be pressure-tightly closed by a stopper. As the container is disposed in the pressure-tightly closable vessel, it is possible to influence, adjust and measure the pressure within and outside the container and thus on both sides of the barrier layer.

It is preferable for the container which is to be investigated to be conditioned outside the closable vessel and thus prior to the beginning of the method. As in known cases, the wall of the container to be investigated is loaded with certain gases for a given period of time. When using the method according to the invention on high-capacity production machines, it is desirable in particular for industrial use if the storage time for finished containers, which is necessary in any case, and the ambient air surrounding such containers, at room temperature, is used for the conditioning operation. In addition it may be desirable for the term conditioning also to be interpreted as meaning the further step of an initial degassing operation, in order more specifically when ascertaining the pressure-time curve to move into similar or preferably even the same pressure ranges in which then measurement is made in respect of the time, within which the pressure rises in the container to the predetermined end pressure due to degassing. That preliminary degassing operation is effected in a short period of time and considerably assists with the measurement procedure.

Because the containers are loaded generally and particularly in the case of industrial application with a mixture of substances, inter alia a mixture of gases, it is preferably provided that, when using simple measuring devices, the sum of a plurality of partial pressures is measured together, and the overall pressure resulting therefrom can be fully successfully used for ascertaining the gradient of the pressure-time curve.

There are the most widely varying vacuum pumps available on the market so that evacuation of the container to be investigated on the one hand (internally) and also the vessel enclosing it on the other hand (externally) can be effected easily and very quickly. It has been found that it is desirable in accordance with the invention if at least one of the spaces is evacuated to about 1 millibar pressure. The first preliminary degassing step in order to achieve the pressure range which is attained for reproducibility of the determination method can be effected below or above the pressure value of 1 millibar, depending on the respective preselected pressure range in which the pressure-time curve is considered to be particularly relevant.

In order to achieve values which can be well reproduced and which are accurate for attainment, a dependency range in which the relationships of pressure and time are substantially linear is picked out of that pressure-time curve. In accordance with the invention therefore, that (limited) range in which the pressure varies linearly in relation to time is picked out of the pressure-time curve. The gradient which is then afforded represents a direct measurement in respect of the quality of the barrier layer. If for example a pressure range of between 3 and 4 mbars is selected, then a greater time interval for attaining that pressure difference between the beginning and the end in the degassing operation means that the quality of the barrier layer is good and vice-versa.

Behind that is the model conception that at the beginning of the determination method the plastic wall of the container to be measured is loaded with gases and possibly also water from the environment up to a certain level of saturation. Upon coating the inside surface of the container to be measured with a barrier, the latter prevents rapid outgassing. Therefore, the time within which the preselected rise in pressure is attained gives a clear indication as to how completely or defectively the barrier layer has prevented degassing of the container wall.

In accordance with the invention it is particularly desirable if, for the planned industrial use, after the evacuation operation, the sum of the partial pressures of all substances emitted from the container wall is measured. There is therefore no need to pay particular attention to a specific partial pressure or for it to be treated in a specific fashion, but it is possible for the pressure of the degassed substances to be measured with a simple standard vacuum measuring tube, for example a capacitance measuring tube. Practice has shown that such a measuring tube only has to measure in the millibar range and does not need to cover other measuring ranges at lower pressure, which are remote therefrom by powers of ten.

The determination method according to the invention does not require the use of high temperatures which possibly cause damage to the wall materials of the container to be measured. There is also no need to use chemical substances in order to influence and possibly destroy the barrier layer or the container wall therebehind. In less than 10 minutes, preferably less than 5 minutes, it is possible to measure the attainment of the preselected pressure difference, and information about the quality of the barrier property can be achieved by way of the determined gradient of the pressure-time curve. The lesser the gradient, that is to say the greater the period of time until the upper pressure end value is attained, the correspondingly higher is the quality of the barrier layer, the evaluation of which as good, adequate or defective is already sufficient.

Alternatively however in accordance with the invention it is also possible with the new method, after the evacuation operation, to measure only the partial pressure of at least one substance emitted from the container wall, in particular a gas. The above-mentioned features of the method according to the invention are sufficient for the measurement of the partial pressure of only one, two or three substances. Such a method can be carried out for example by means of a mass spectrometer which admittedly itself measures in a pressure range of the order of magnitude of about $10^{-6}$ mbars which however can also be connected by a pump disposed in parallel, preferably a turbomolecular pump and a preliminary pump, to measuring lines whose pressure is in the range of between 1 and 10 millibars. With a quadrupole measurement head, a mass spectrometer permits the measurement of various peaks with different atomic units of mass. In particular the peaks for for example water, nitrogen or oxygen are of interest here. The method according to the invention then recommends measurement of the time difference, within which the line in question (in English often also referred to as the 'peak') has reached a preselected growth in its intensity relative to a given initial value or relative to another line. Here admittedly there is an intensity-time curve which in principle however corresponds equally to the above-mentioned pressure-time curve. That intensity-time curve also includes linear ranges. In that way it is again possible to infer the quality of the barrier layer from the time duration, but now this is for a given substance.

In connection with the last-mentioned embodiment of the determination method according to the invention, it is desirable, in a further advantageous configuration, if the partial pressure of at least one substance which is emitted by the container wall and which is relevant in terms of influencing the taste of the filling of the container is measured. The end consumer can at the present time already buy fizzy water, which is mixed to a greater or lesser degree with $CO_2$, in plastic bottles which are similar to glass bottles, but which inter alia have the advantage thereover of being of lower weight. In the case of poor processing the end consumer recognises the unpleasant 'plastic taste' if the water poured out of such a bottle tastes of 'plastic'. In the meantime, investigations were conducted to establish the substances which are relevant for that adverse effect on taste, and such substances were established. Those substances are known and can be detected with the above-mentioned mass spectrometer. A known representative of such substances is acetyladehyde. Measurement of the partial pressure of such a substance which is relevant in terms of taste, in a filling content material, for example fizzy water, makes it possible to determine the quality of the barrier. More specifically, if such a fizzy drink bottle of plastic material is provided on its inside surface with a barrier layer, for example on a quartz basis, then it is possible from time to time to prevent substances which are relevant in terms of taste and which are in the plastic wall of the container from escaping into the content of the bottle. It will be appreciated that the degree of prevention is to be as high as possible and can be detected with the method according to the invention of the kind just described above.

The method according to the invention is adjudged to be particularly advantageous if, in a further configuration of the invention, the quality of the barrier layer of a reference container is used for calibrating the gradient of the measured pressure-time curve. There are very accurate measurement methods for the barrier quality of a container, although entailing the disadvantage that between 2 hours and 5 days are necessary to scientifically ascertain the precise calibrated value. If now such a reference container which has already been measured is used in implementing the method according to the invention, then it has a certain gradient in the measured pressure-time curve, and that gradient for example stands for the assessment 'good'. In accordance with the invention, it is now possible to determine the quality of the barrier layer of the container to be measured, by comparison with the reference container. In accordance with the invention, when omitting numerous conditions and features of scientifically exact measurement methods, it is sufficient to obtain the gradient of the pressure-time curve, which can be measured in a comparatively short time, and compare it to that of an exactly measured reference container.

The determination method according to the invention can be still further influenced in terms of accuracy and reproducibility in that, in accordance with the invention, all containers to be subjected to the determination method are uniformly loaded with molecules in the conditioning time. It is known that the degree of saturation and therewith the measurement results depend on the preliminary treatment in the conditioning time. Therefore the endeavour is made to subject all containers which are to be investigated to uniform preliminary treatment. In accordance with the above-mentioned model conception the user of the method will load the walls of the containers to be investigated, uniformly with the available molecules, for example he will saturate them.

It is desirable in accordance with the invention if the container and the pressure-tightly closable vessel are evacuated in about 1 minute. When using simple vacuum pumps practical tests have given that value which is certainly welcomed in industrial use. That is fully consistent with the fact that the evacuation operation can also be attained in a shorter time, when using stronger vacuum pumps.

In that respect it was further found that it is desirable in accordance with the invention if degassing and measurement of the at least one partial pressure last overall less than 8 minutes, preferably 6 minutes and quite particularly preferably about 4 minutes. If the volume of the structure for carrying out the method according to the invention is fixed, the above-mentioned time values can already be achieved when using simple measuring devices. After the approximately 1-minute evacuation step, it may be sufficient to implement degassing for a period of about 2 minutes in order even in the higher ranges of the pressure difference to find the measurement range which is being contemplated in the pressure-time curve, for example the measurement range between 6 millibars and 6.5 millibars. Good linearity between pressure and time has been found here and satisfactory measurement results have been achieved. The time difference in which for example the pressure has risen from 6 millibars to 6.5 millibars is measured. That measurement can be achieved within 1 minute. Overall therefore a total time of about 4 minutes is involved in evacuation, degassing in the lead-in time to achieve the desired measurement range and thereafter the measurement time. That is a surprising advantage in comparison with the hitherto necessary time of about 2 hours or somewhat less.

The above-described operation of determining the quality of the barrier layer was effected by measurement of the partial pressures after the pressure-tightly closable vessel and the container disposed therein were evacuated. It will be appreciated that some time is required for that evacuation operation, between 2 and 3 seconds in tests which were successfully conducted, in accordance with the invention. The above-described operation of measuring the partial pressures is then effected in the above-mentioned range of the pressure-time curve, in which the pressure varies linearly in relation to time. As mentioned above, the resulting gradient is a direct measurement in terms of the quality of the barrier layer. That measurement method applies both in respect of barrier layers which are on the inside surface of a container and also—in other embodiments—on the outside surface of a container.

Based on the same model conception, it is also surprisingly possible, in accordance with an additional consideration, to carry out a kind of pre-measurement or indication measurement which is based on the same method according to the invention. In continuous production with a high-capacity machine for example 10,000 PET bottles per hour can be produced, in which case a barrier layer is applied to the inside surface of the bottle or also to the outside surface thereof, in a coating process. It will be appreciated that production faults can unexpectedly occur, in which case for example some PET bottles (containers) produced are not provided with a barrier layer, due to a defective coating apparatus. That is admittedly detected by the foregoing quality measurement procedure, but it is possible for the coating process to be influenced more rapidly if any defects are detected more quickly. That is advantageously effected if the products, for example the PET bottles, are investigated in measurement channels immediately after production.

If now in accordance with a further advantageous configuration of the invention, in the evacuation operation, the sum of all partial pressures of the gas disposed in the container or outside same and of the substances emitted from the container wall are measured, that can be effected in a substantially shorter time. That preliminary measurement or indication measurement is not intended to replace the above-described quality measurement procedure. It can however supplement it, to great advantage. For example, the failure of a coating apparatus can be detected in a substantially shorter time. Then, an indication or a coarse measurement result is obtained in a shorter time after production, from which it is possible to establish with a sufficient level of certainty whether the product, the coated container in question, is provided with a barrier layer which satisfies the more accurate quality measurements.

The basic concept of this further development in accordance with the invention is that evacuation of the closable vessel and the container disposed therein can already be used for a measurement operation or a pressure measurement procedure can be carried out in that initial time in which degassing or evacuation is first effected. In accordance with the model already discussed in the opening part of this specification, the plastic wall of the container to be measured is loaded with substances, in particular gases and possibly also water, from the environment. After that loading operation, degassing takes place. When coating the inside or outside surface of the container to be measured with a barrier, the latter prevents rapid outgassing, when of adequate quality. Therefore, the time within which a preselected degree of evacuation is reached also already gives a clear indication, during evacuation or degassing, as to whether the barrier layer has prevented degassing of the container wall, with a sufficient level of quality.

In the evacuation operation however it is not only the partial pressures of the substances emitted from the container wall that are measured, but also the partial pressures of that gas which is on the side where the wall is coated. If a PET bottle is coated on its inside surface, then the partial pressures of the gas in the container are also measured. If the coating is on the outside surface of the container, for example the PET bottle, then the partial pressures of the gases outside the PET bottle are also measured. That measurement method operates satisfactorily if the sum of all partial pressures of the gases is measured. A pressure measuring device connected to the volume of the vessel, for example a capacitance measuring tube, is used for measurement of the sum of the gas partial pressures, that is to say for the actual pressure measurement procedure.

It is further desirable in accordance with the invention if the partial pressures are measured after a fixed time and compared to a target pressure value. Operation begins with carrying out the method at the beginning of a pressure-time curve and the partial pressures are measured at a time which is fixed similarly to a calibration step. In that case, the measurement value in respect of the partial pressures is compared to a target pressure value, for which it is also possible to apply a certain range. If after the fixed time the measurement operation gives a pressure value which is in the proximity of the target value, it is concluded that the barrier layer is of adequate quality. The pressure range is of the order of magnitude of $1/100$ mbar.

Alternatively in accordance with the invention it is advantageously also possible to measure the time in which a predetermined target partial pressure is reached. If for example the target partial pressure is reached only after an excessively long time, it can be concluded that the barrier layer is of defective quality.

The new method for preliminary measurement or indication measurement may admittedly involve fluctuations in comparison with the above-specified main method when measuring the rise in pressure, which fluctuations are in the range of 20% in comparison with precise measurement, in tests which were carried out. That scatter range is harmless however if it is possible nonetheless to clearly establish a quality trend. That scatter range is afforded for example due to fluctuations in the efficiency of the evacuation pumps. The efficiency thereof admittedly has an influence on indication measurement. However, in a considerably shorter time, this procedure affords preliminary measurements which permit qualitative information in respect of each bottle (container) produced. In the above-described quality measurement procedure in the range of the rising pressure curve, the process is independent of the pump efficiency of the evacuation phase. The more accurate quality measurement as described in the opening part of this specification is therefore not replaced by the preliminary or indication measurement procedure. It only supplements it for conclusions about the coating process can be drawn from the preliminary measurement operation at a very early stage and the coating process can thus be suitably controlled.

In accordance with the invention, for carrying out the method in accordance with one of the above-discussed embodiments, it is provided that a first measuring tube is passed out of the internal space of the container through a plug or stopper to outside the closable vessel and connected to a pressure measuring device and by way of at least one valve to a vessel emptying conduit connected to a vacuum pump. For our own envisagement the container can be considered as a plastic bottle with a stopper, through which a first measuring tube is passed. That affords access to the internal space in the container, it can be evacuated and the pressure obtaining therein can be measured. The latter is effected by way of a connected pressure measuring device which is disposed outside the closable vessel. The first measuring tube can be passed out of the internal space of the container and also the internal space of the closable vessel, to the exterior where the pressure measuring device is disposed.

In addition, in accordance with the invention, in the apparatus being considered here, there is connected a vacuum pump which is in communication with the first measuring tube by way of at least one valve. Because there is also a wish to evacuate outside the closable vessel, connected to that vessel is a vessel emptying conduit which is also coupled to the vacuum pump by way of connecting conduits. That structure is simple and allows simple measuring apparatuses to be used as well as quality determination in respect of the barrier layer to be measured, in a short time, preferably in less than 5 minutes. If a particularly simple capacitance measuring tube is used for the pressure measurement procedure, it is already possible to attain the above-mentioned advantages, in which respect consideration is given in particular to the sum of all partial pressures of the substances emitted from the container wall.

If, in another embodiment of the apparatus, the pressure measuring device is a mass spectrometer which is connected to the first measuring tube by way of a protective valve, it is possible to measure the pressure build-up for individual substances which are emitted from the container wall. It was surprisingly found for example that a substance measured by means of the mass spectrometer with u=17 atomic units of mass can be correlated with the later occurrence of the known plastic taste, already referred to above, in the contents of the container (water in a fizzy drink bottle). The method according to the invention can then also be carried out quickly and simply, in terms of substances which are relevant to taste, with a mass spectrometer.

If, in a further configuration of the invention, at least the first measuring tube is short and comprises stainless steel, fewer faulty measurements are obtained, for only few substances can evaporate out of the material of the stainless steel, and make a contribution in terms of pressure measurement.

The endeavour therefore is to make the first measuring tube and the further tubes necessarily connected thereto as short as possible.

In accordance with the invention moreover a measuring valve and a finely regulatable valve, such as for example a needle valve, can be connected in series between the connecting location at which the vessel emptying conduit is connected to the closable vessel and the first measuring tube. While the measuring valve is required to permit measurement (when the measuring valve is closed) the use of the needle valve advantageously permits the use of only one single vacuum pump. Then, with that pump, the closable vessel on the one hand (external space around the container) and also the internal space of the container to be measured can be evacuated with precisely that one pump. More specifically, the needle valve permits regulation of the gas flow in the pumping-out operation; in other words, regulation of the gas flow out of the container to be measured, in relation to the gas flow out of the closable vessel in which the container is arranged. The pressures inside and outside the container to be measured should more specifically desirably be similar. Major pressure differences are to be avoided. If the pressure outside the container were considerably greater than inside, it will be appreciated that there would be a fear of the container collapsing; conversely the plug in the container to be measured could be urged out of the opening thereof or indeed the container itself could be caused to burst if the pressure outside the container, namely within the vessel to be closed off, were considerably lower than the internal pressure in the container (an order of magnitude difference).

Figure 2:
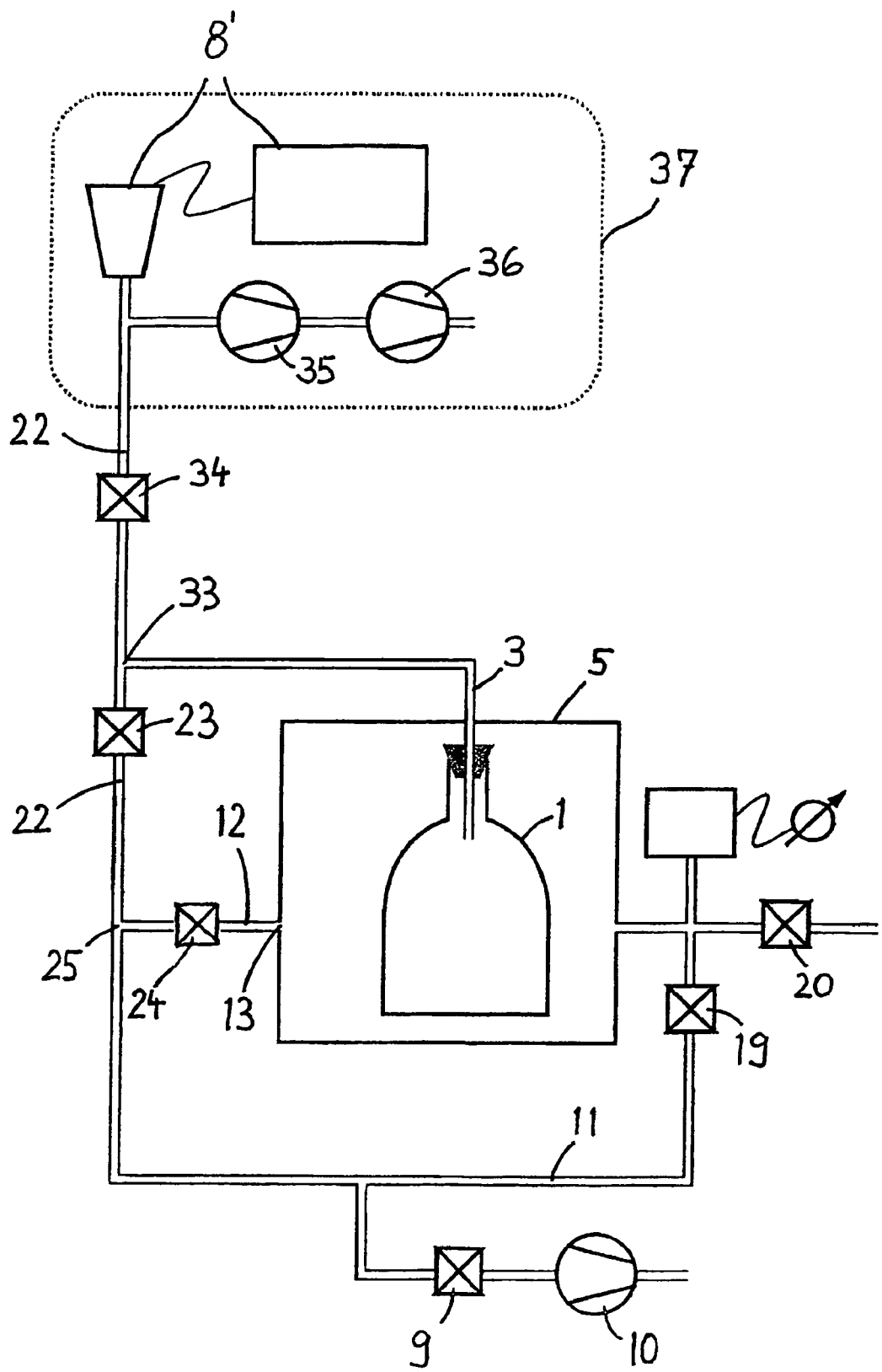
Figure 3:
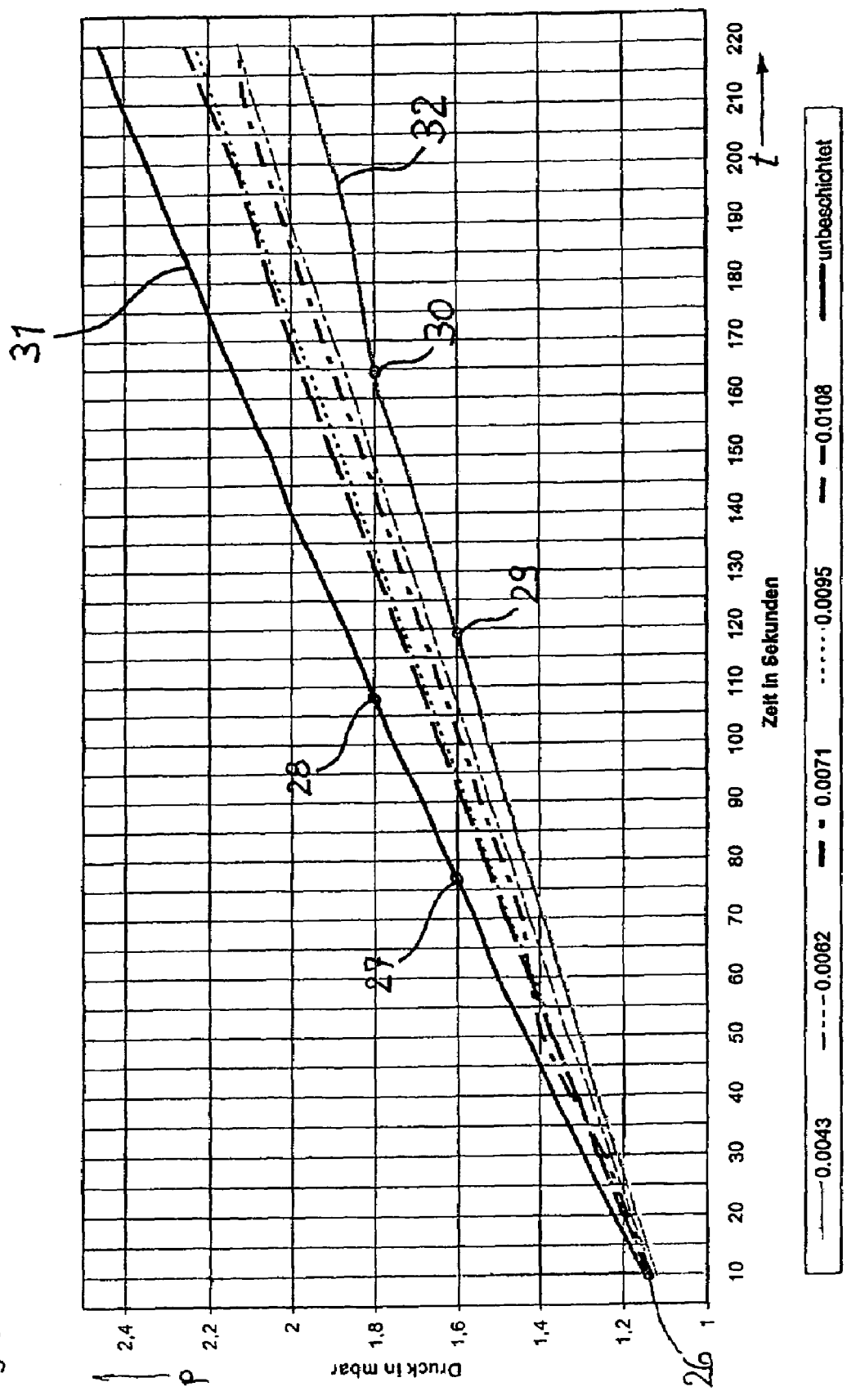
Figure 4A:
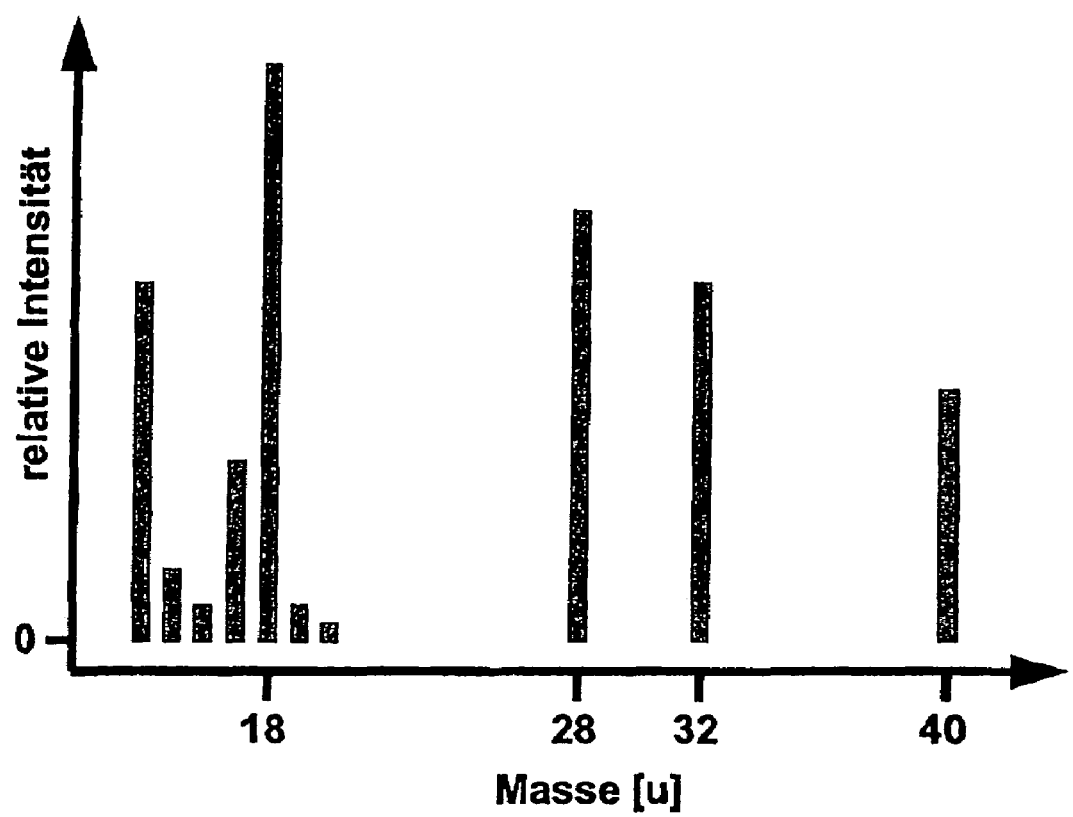
Figure 4B:
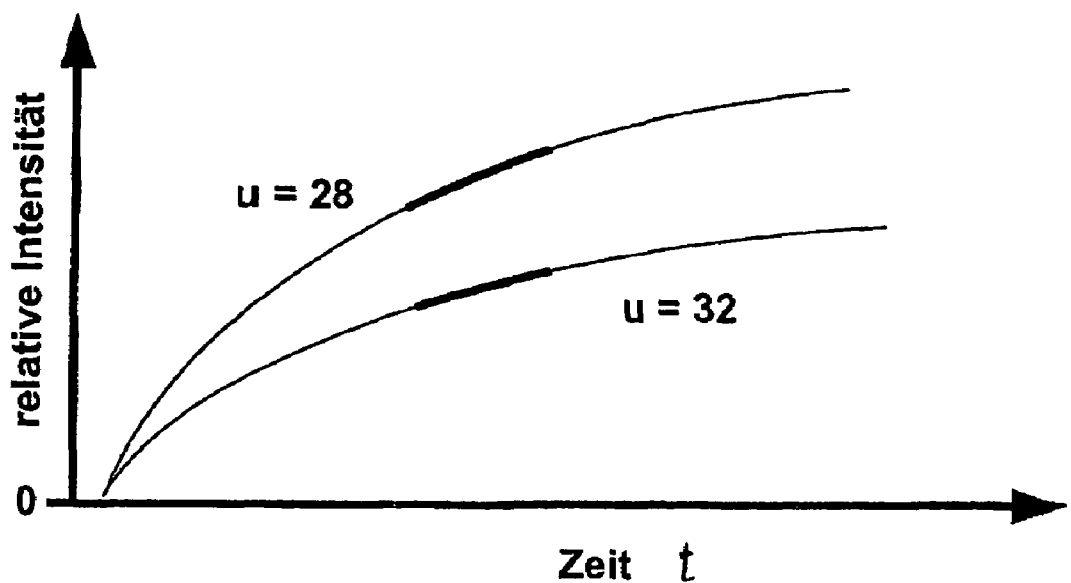
Figure 5:
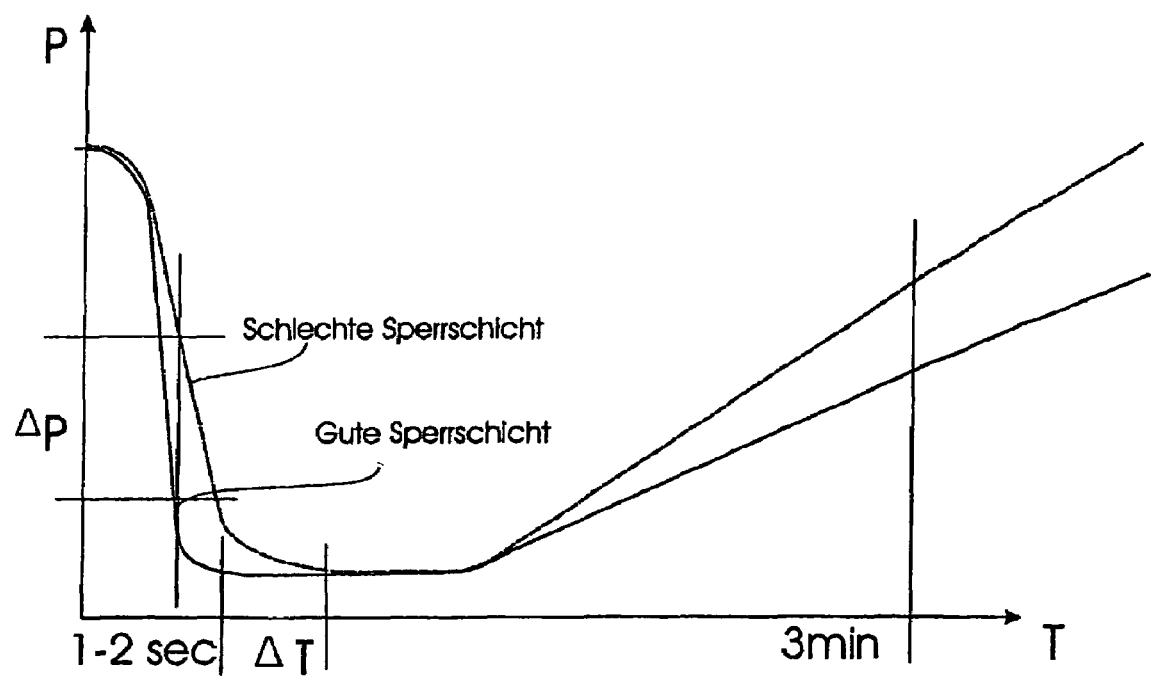

Further advantages, features and possible uses of the present invention will be apparent from the description hereinafter of preferred embodiments of the invention with reference to the drawings in which:

FIG. 1 diagrammatically shows a first apparatus for carrying out the determination method according to the invention, FIG. 2 shows a similar apparatus to FIG. 1 but using a mass spectrometer for measuring the pressure-time curve or intensity-time curve, FIG. 3 shows the pressure-time curve for different substances degassed out of the container wall, FIG. 4a diagrammatically shows the measurement representation in a mass spectrometer with lines for different atomic units of mass, FIG. 4b shows an intensity-time curve for two selected gases which were measured in the mass spectrometer of FIG. 2, and FIG. 5 shows a similar pressure-time curve to FIG. 3, but also showing the initial degassing range.

The container 1 to be measured is shown in the form of a water bottle of plastic material without content (water) and is closed in its bottle neck by a stopper 2, through which a first measuring tube 3 is passed. The lower open end 4 of the first measuring tube 3 ends approximately at the center of the container 1 which is disposed in a pressure-tightly closable vessel 5 at a spacing from the walls thereof. The first measuring tube 3 leads out of the internal space 6 of the container 1 through the stopper 2 and through the upper wall of the closable vessel 5 upwardly to terminate at the connection 7 of the pressure measuring device 8 which is in the form of a capacitance measuring tube.

A vacuum pump 10 is connected by way of an outlet valve 9 to a ring conduit 11, by means of which the closable vessel 5 can be evacuated by means of the gas emptying conduit 12. For that purpose, there is provided a connection location 13 to the closable vessel 5, through which the vessel emptying conduit 12 is in direct communication with the vessel 5 on the one hand and the ring conduit 11 on the other hand so that, when the valve 9 is opened and the vacuum pump 10 is switched on, the internal space 14 of the closable vessel 5 can be evacuated.

There is also in the outside wall of the closable vessel 5 a further connecting location 15 which is connected to a venting conduit 16 and a measuring (17) and also suction conduit (18). The suction conduit 18 can be connected to the ring conduit 11 by way of an auxiliary valve 19. Upon being opened a venting valve 20 permits venting of the internal space 14 of the vessel 5. Connected to the measuring conduit 17 is a simple pressure measuring device 21 which in the present structure operates with a Pirani tube.

Finally the connecting conduit 22 connects the first measuring tube 3 to the ring conduit 11 by way of two valves. Those two valves which are connected in series are a measuring valve 23 and a needle valve 24. The ring conduit 11, the vessel emptying conduit 12 and the connecting conduit 22 provided with the two valves 24 and 23 come together at the connecting point 25.

In operation, when the venting valve 20 is closed and the valves 19, 23, 24 and 9 are open, the container 1, by way of the first measuring tube 3, and also the closable vessel 5, are evacuated. No major pressure difference occurs between the internal space 6 of the container 1 and the internal space 14 of the vessel 5. The pressure in the internal space 14 of the vessel 5 is measured by way of the pressure measuring device 21. The needle valve 24 provides for regulation of the gas flows from the internal space 6, in relation to those from the internal space 14.

After closure of the measuring valve 23 and preferably also the valves 9 and 19 the pressure in the internal space 6 of the container 1 is measured by way of the capacitance measuring tube 8.

If attention is directed to FIG. 3, it is then assumed in practice in this embodiment that a pressure of about 1.15 mbar (first measuring point 26) is measured at the time t=10 seconds. The upper curve 31 represents the pressure-time curve of an uncoated bottle/container.

After closure of the measuring valve 23 the pressure measuring device 8 which is in the form of a capacitance measuring tube reaches a pressure value of 1.6 mbar, after 77 seconds, at the second measuring point 27. On the assumption that from here in a certain range there is a linear dependency between pressure and time, a period of 31 seconds is waited and then, when the pressure of 1.8 mbar is reached, at the third measuring point 28, a time of 120 seconds is measured. The gradient of that curve (straight line) makes it possible to state that the quality of the barrier layer is defective. The curve 31 represents the uncoated container.

In comparison therewith the lower curve 32 represents the pressure-time relationship of a container 1 provided with a good barrier layer. Between the fourth measuring point 29 at which the initial pressure of 1.6 mbar is reached and the fifth measuring point 30 at which the chosen end point of 1.8 mbar is reached, there is a time difference of 45 seconds, showing that this shallower gradient indicates good barrier properties.

After such a measurement procedure which lasted about 4 minutes, the valves 9 and 19 are closed and the internal space 14 of the vessel 5 is vented by way of the opened venting valve 20.

Thereafter the measurement operation is repeated for the next container 1.

The apparatus of FIG. 2 differs from that shown in FIG. 1 in only two respects:

1. The first difference is that the first measuring tube 3 is connected at a further connection location 33 to the connecting conduit 22 which by way of a protective valve 34 forms the communication with the pressure measuring device 8' which is in the form of a mass spectrometer. A turbomolecular pump 35 with downstream-connected series pump 36 provides for a reduction in the tube internal pressure in the connecting conduit 22 between the protective valve 34 and the mass spectrometer 8'.

2. If consideration is given to the connecting conduit 22 from the connection location 13 at the vessel 5 to be closed and the further connection location 33 between the protective valve 34 and the measuring valve 23, then admittedly the measuring valve 23 and the needle valve 24 are again in series. The needle valve 24 however is in the vessel emptying conduit 12 between the connection location 13 and the connecting point 25. In this position also the needle valve performs the same function and involves the same aim as referred to above, also with reference to FIG. 1.

The display of the mass spectrometer 8' shows the individual peaks with the various atomic units of measurement as shown in FIG. 4a. Here peaks are shown at u (X-axis), for example equal to 14, 18, 28, 32 and 40. The peaks which are not identified in greater detail correspond for example inter alia to water and increase slowly in the course of measurement in relation to time, as is shown for example by the illustration in FIG. 4b. Relative peak intensity is plotted therein, in relation to time t. A curve (upper) is shown for u=28 and a further curve (lower) is shown for u=32. Both have the linear range which is emphasised in the drawing so that the quality of the barrier for the substance with u=28 and so forth can be determined from the gradient of that curve.

FIG. 5 shows a similar pressure-time curve to FIG. 3. In FIG. 5 pressure p is again plotted in relation to time T. In this case two curves are considered: the curve shown in solid line is that for a good barrier layer and the curve shown with a broken line is that for a poor barrier layer. The straight limbs shown in the right-hand part correspond to the curves in FIG. 3. Actual quality measurement is therefore effected only in that range after evacuation has been implemented and the lower horizontal level range of the two curves in FIG. 5 is reached.

FIG. 5 now additionally also shows the initial degassing range at the left. In carrying out the method it is possible to start from the zero point and the pressure is reduced in the degassing or evacuation operation. If that reduction in pressure takes place only more slowly in accordance with the broken-line curve, then this indicates a poor barrier layer. More specifically, the poor barrier layer is not so capable of retaining substances, for example gases, which have been loaded into the wall.

The curve which is shown with solid lines and which indicates a good barrier layer extends correspondingly more steeply. That barrier layer allows the pressure on the side with the coating to fall more quickly because not so much loaded-in gases enter through the layer into the space which is delimited by the layer. In the example illustrated here, a given lower value in the pressure range Δp is reached after between 1 and 2 seconds. The upper pressure limit point is even already reached shortly before that. If we take the embodiment in which the partial pressures are measured after a fixed time, then it must be noted whether the measured partial pressures are in the allowed pressure range Δp, that is to say above the lower limit value thereof.

If on the other hand there is a wish to achieve a predetermined target partial pressure, then in accordance with the second embodiment it is possible to measure that time in which the target pressure is reached. Here the time ΔT is plotted on the abscissa. If for example the lower limit value of the pressure is reached within the time internal ΔT or previously, then this involved measuring a good barrier layer.

Quality measurement in respect of the containers produced is effected irrespective of that preliminary or indication measurement in a time of about 3 minutes from the beginning of evacuation.

List of References:
1 container
2 stopper
3 first measuring tube
4 lower open end of the measuring tube
5 pressure-tightly closable vessel
6 internal space of the container
7 connection of the pressure measuring device
8 or 8' pressure measuring device comprising diagrammatically illustrated measuring tube and display device
9 outlet valve
10 vacuum pump
11 ring conduit
12 vessel emptying conduit
13 connection location
14 internal space of the closable vessel
15 further connection location
16 venting conduit
17 measuring conduit
18 suction conduit
19 auxiliary valve
20 venting valve
21 pressure measuring device comprising diagrammatically illustrated Pirani measuring tube and display device
22 connecting conduit
23 measuring valve
24 finely regulatable valve
25 connecting point
26 first measuring point
27 second measuring point
38 third measuring point
29 fourth measuring point
30 fifth measuring point
31 upper curve (uncoated)
32 lower curve (with good barrier)
33 further connection location
34 protective valve
35 turbomolecular pump
36 series pump
37 mass spectrometer unit

The invention claimed is:

1. A method for determining the permeation of a barrier layer on the surface of a container (1), in which the container (1) is put into a pressure-tightly closable vessel (5), it is left to degas after a conditioning time on the side with the barrier layer, the pressure in relation to time is measured and permeation of the barrier layer is determined from those measurement data, characterised in that the pressure-tightly closable vessel (5) and the container (1) disposed therein are evacuated, the pressure of a plurality of substances emitted from the container wall is measured, the gradient of the pressure-time curve based on the change of the pressure in relation to time is determined and the quality of the barrier layer is ascertained as a direct measurement with reference to the pressure-time curve, and a first measuring tube (3) is passed out of the internal space (6) of the container (1) to outside the closable vessel (5) and is connected to a pressure measuring device (8; 8') and is connected by way of at least one valve (23, 24, 9) to a vessel emptying conduit (12) connected to a vacuum pump (10), wherein a measuring valve (23) and a finely regulatable valve (24) are connected in series between a connection location (13) of the vessel emptying conduit (12) to the closable vessel (5) and the first measuring tube (3).

2. A method as set forth in claim 1 characterised in that the quality of the barrier layer of a reference container is used for calibrating the gradient of the measured pressure-time curve.

3. A method as set forth in claim 1 characterised in that in the conditioning time all containers (1) to be subjected to the determination method are uniformly loaded with molecules.

4. A method as set forth in claim 1 characterised in that the container (1) and the pressure-tightly closable vessel (5) are evacuated in about one minute.

5. A method as set forth in claim 1 characterised in that degassing and measurement of at least one partial pressure lasts in total less than 8 minutes, preferably 6 minutes and quite particularly preferably about 4 minutes.

6. A method as set forth in claim 1 characterised in that after evacuation the partial pressures of all substances emitted from the container wall are measured.

7. A method as set forth in claim 1 characterised in that after evacuation the partial pressure of at least one substance emitted from the container wall, in particular gas, is measured.

8. A method as set forth in claim 7 characterised in that the partial pressure of at least one substance which is emitted from the container wall and which is relevant in terms of the container filling being influenced in its taste is measured.

9. A method as set forth in claim 1 characterised in that in the evacuation step the sum of all partial pressures of the gas in the container (1) or outside same and the substances emitted from the container wall are measured.

10. A method as set forth in claim 9 characterised in that the partial pressures are measured after an established time and compared to a target pressure value (Δ p).

11. A method as set forth in claim 9 characterised in that the time in which a predetermined target partial pressure is reached is measured.

12. An apparatus for carrying out a method for determining the permeation of a barrier layer on the surface of a container (1), in which the container (1) is put into a pressure-tightly closable vessel (5), it is left to degas after a conditioning time on the side with the barrier layer, the pressure in relation to time is measured and permeation of the barrier layer is determined from those measurement data, characterised in that the pressure-tightly closable vessel (5) and the container (1) disposed therein are evacuated, the pressure of a plurality of substances emitted from the container wall is measured, the gradient of the pressure-time curve based on the change of the pressure in relation to time is determined and the quality of the barrier layer is ascertained as a direct measurement with reference to the pressure-time curve, the apparatus characterized in that a first measuring tube (3) is passed out of the internal space (6) of the container (1) to outside the closable vessel (5) and is connected to a pressure measuring device (8; 8') and is connected by way of at least one valve (23, 24, 9) to a vessel emptying conduit (12) connected to a vacuum pump (10), wherein a measuring valve (23) and a finely regulatable valve (24) are connected in series between a connection location (13) of the vessel emptying conduit (12) to the closable vessel (5) and the first measuring tube (3).

13. Apparatus as set forth in claim 12 characterised in that the pressure measuring device (8) is a capacitance measuring tube.

14. Apparatus as set forth in claim 12 characterised in that the pressure measuring device (8') is a mass spectrometer which is connected to the first measuring tube (3) by way of a protective valve (34).

15. Apparatus as set forth in claim 12 characterised in that at least the first measuring tube (3) is short and comprises stainless steel.

16. Apparatus as set forth in claim 12 characterised in that the gradient of the pressure-time curve is determined within a predetermined pressure range after an initial degassing of the evacuated container.

17. Apparatus as set forth in claim 12 characterised in that the first measuring tube (3) is passed out of the internal space (6) of the container (1) through a stopper (2) to outside the closable vessel (5) [and connected to a pressure measuring device (8; 8') and by way of at least one valve (23, 24, 9) to a vessel emptying conduit (12) connected to a vacuum pump (10)].

18. Apparatus as set forth in claim 12 characterised in that the pressure measuring device (8) is a capacitance measuring tube.

19. Apparatus as set forth in claim 12 characterised in that the pressure measuring device (8') is a mass spectrometer which is connected to the first measuring tube (3) by way of a protective valve (34).

20. Apparatus as set forth in claim 12 characterised in that at least the first measuring tube (3) is short and comprises stainless steel.

* * * * *

UNITED STATES PATENT AND TRADEMARK OFFICE
CERTIFICATE OF CORRECTION

| | | |
|---|---|---|
| PATENT NO. | : 7,121,135 B2 | Page 1 of 1 |
| APPLICATION NO. | : 10/478060 | |
| DATED | : October 17, 2006 | |
| INVENTOR(S) | : Rodney Moore | |

It is certified that error appears in the above-identified patent and that said Letters Patent is hereby corrected as shown below:

On the Title page:

Item (73) Assignee: "Tetra Laval Holdings & Fiance S.A." should read --Tetra Laval Holdings & Finance S.A.--;

In the Specification:

Col. No. 11, line 48, "38 third measuring point" should read -- 28 third measuring point --.

Signed and Sealed this

Twenty-second Day of May, 2007

JON W. DUDAS
*Director of the United States Patent and Trademark Office*